(12) United States Patent
Langsch

(10) Patent No.: US 6,557,397 B2
(45) Date of Patent: May 6, 2003

(54) PROCESS AND DEVICE FOR EVALUATING THE QUALITY OF A PRINTING INK

(75) Inventor: Robert Langsch, Ortschschwaben (CH)

(73) Assignee: Maschinenfabrik Wifag (CH)

( * ) Notice: Subject to any disclaimer, the term of this patent is extended or adjusted under 35 U.S.C. 154(b) by 0 days.

(21) Appl. No.: 10/122,840

(22) Filed: Apr. 11, 2002

(65) Prior Publication Data

US 2002/0148287 A1 Oct. 17, 2002

(30) Foreign Application Priority Data

Apr. 12, 2001 (DE) .......................... 101 18 604

(51) Int. Cl.⁷ ................................. G01L 3/00
(52) U.S. Cl. .................... 73/54.01; 73/61.43; 73/61.44; 73/862.08; 73/73
(58) Field of Search .............................. 73/54.01, 61.41, 73/61.43, 61.44, 54.23, 54.28, 83, 862.08

(56) References Cited

U.S. PATENT DOCUMENTS 4,239,543 A * 12/1980 Beasley .................. 106/31.43
4,580,143 A * 4/1986 Larsen ......................... 347/7
5,376,169 A * 12/1994 Hotomi et al. ........... 106/31.73
5,987,970 A * 11/1999 Ball ........................... 73/54.28
6,277,780 B1 * 8/2001 Beckler et al. ............. 423/299

FOREIGN PATENT DOCUMENTS

| DE | 2531474 A | * | 2/1977 | ........... G01N/11/14 |
| DE | 3410393 A | * | 9/1985 | ........... C09D/11/02 |
| DE | 36 02 309 | | 7/1987 | |

* cited by examiner

Primary Examiner—Daniel S. Larkin
Assistant Examiner—David Rogers
(74) Attorney, Agent, or Firm—McGlew and Tuttle, P.C.

(57) ABSTRACT

A process for evaluating the quality of a printing ink is provided, wherein a defined quantity of the printing ink is stirred; a force or torque to be applied during the stirring is measured, and a defined quantity of moistening agent is added to the ink at a defined point in time. A device for evaluating the quality of the printing ink is also provided with a container for the printing ink; a stirring device, with which an ink filled into the container can be stirred; a measuring device for measuring the force to be applied by the stirring device or the torque to be applied; a moistening agent supply and a control, which actuates the feed of moistening agent such that a predetermined quantity of moistening agent is introduced into the container at a defined point in time.

23 Claims, 14 Drawing Sheets

PROCESS AND DEVICE FOR EVALUATING THE QUALITY OF A PRINTING INK

FIELD OF THE INVENTION

The present invention pertains to a process and a device for evaluating the quality or the analysis of a printing ink, especially for evaluating the suitability of a printing ink being investigated for printing, especially offset printing.

BACKGROUND OF THE INVENTION

Besides the printing materials, the ink used as well as the behavior of the ink in conjunction with water greatly affect the printing result as well as the stability of the printing process running over a rather long time and under different operating conditions. A printing ink used must be able to take up water to a certain extent especially for offset printing.

The so-called Surland test, according to which 50 g of ink are stirred with 50 g of water, is known for determining the water uptake capacity of an ink. The excess water not taken up by the ink is poured off after 5 minutes. If the ink has taken up 10 to 15 g of water during these 5 minutes, it is considered to be good according to the Surland test, whereas the ink is considered to be unsuitable for offset printing if it has taken up more than 20 g of water. FIG. 11 shows the moistening agent uptake behavior of different inks A through F used over time, where it can be seen that the inks A through D and F have taken up approximately equal quantities b of moistening agent after exposure to a water bath for the duration a of 5 minutes, so that the corresponding characteristics all pass through the equilibrium point P. The ink E shows a relatively poor water uptake behavior and is therefore unsuitable for offset printing.

Moreover, manual stirring tests are known for determining the saturation limit of the moistening agent uptake capacity of an ink; whether the amount of the stirring effort needed is great or small is assessed in these manual stirring tests by instinctive feeling only. In particular, it is not possible to predict whether a certain printing ink can indeed be used in offset printing or not.

A device for determining the emulsification behavior and the saturation limit of an ink is available commercially from the firm of Novocontrol under the name "Lithotronic Emulsification Tester." This device has a container for an ink sample, into which extends a stirring device in order to stir an ink filled into it, and the torque occurring during the stirring is measured. According to the test procedure proposed by the manufacturer of the device, the ink sample is first stirred at 1,200 rpm until the torque measured becomes constant. Water is then added continuously at a rate of 1.5 to 3 g per minute. When the torque collapses, the saturation limit of the ink is reached, i.e., water added additionally is no longer taken up by the ink, and it thus permits an easier run of the testing device.

FIG. 12 shows a test result obtained with this device, where two different inks A and B were introduced into the device and stirred continuously for 5 minutes, so that the torque was constant at about 230 mNm and the temperature was constant at about 40° C. The continuous addition of water was started after 5 minutes. As can be seen from FIG. 12, the torque to be applied for stirring increases in the case of ink A for about 11 minutes after the beginning of the addition of water and then gradually collapses. The amount of water taken up by the ink sample can be determined from the amount of water added during this time, i.e., the saturation limit of the ink can be determined. The torque to be applied during stirring remains constant in the case of the ink B tested for about 4 minutes after the beginning of the addition of water and then decreases continuously. Thus, a saturation limit can also be determined for ink B, and it can be qualitatively read from the diagram that the water uptake capacity of ink B is lower than that of ink A. As another parameter, it can be read from the diagram in FIG. 12 that ink A has an increasing wet viscosity, i.e., the viscosity increases during the addition of water, whereas ink B has a decreasing wet viscosity, i.e., it is becoming less viscous during the addition of water. Even though this ink testing process makes possible a certain standardization during the testing of different inks, the parameters determined, namely, the wet viscosity behavior and the saturation limit, are essentially unsuitable for making statements on whether an ink being tested leads to good or poor results in the printing process.

SUMMARY OF THE INVENTION

The primary object of the present invention is to provide a process and a device with which parameters for evaluating the quality of an ink can be determined. In particular, processes and a device shall be provided according to the present invention which make it possible to make a statement on whether an ink is suitable or unsuitable for a printing process and to determine where problems will occur during the use of that ink.

According to the invention, a process is provided for evaluating the quality of a printing ink. A defined quantity of the printing ink is stirred. A force or energy applied during stirring or a torque applied is measured. A defined quantity of moistening agent is added to the ink at a defined time, preferably all at once.

According to another aspect of the invention, a process is provided for determining the moistening agent content in an ink sample. The saturation limit of a fresh ink is determined. A moistening agent is added to the ink sample during ongoing stirring. The point in time at which the force to be applied for stirring or the torque to be applied drops below a predetermined limit is measured. The moistening agent content is determined from the determined saturation limit of the fresh ink and the time period determined.

According to still a further aspect of the invention, a device for evaluating the quality of a printing ink is provided including a container for the printing ink, a stirring device, with which an ink filled into the container can be stirred, a measuring device for measuring the force to be applied by the stirring device or the torque to be applied and a moistening agent supply. A control actuates the moistening agent supply such that a preset quantity of moistening agent is introduced into the container at a defined point in time.

The present invention is based on the following discovery, which will be described below with reference to FIG. 13. FIG. 13 schematically shows the surface of a printing plate, where an ink-attracting, smooth area Z and a water-attractive, rough or porous area Y are shown next to one another. Water is first applied to the printing plate during the printing process prior to the printing operation proper, and this lies on the smooth area Z as a thin film of water and is taken up to a comparatively greater extent by the rough or porous area. An ink is subsequently applied to the printing plate. The ink takes up the thin film of water lying on the ink-attracting areas Z of the printing plate and is thus deposited on these areas. However, the rough area Y has taken up more water than the smooth area Z and acts as a reservoir of water because of its uneven surface finish or porosity. As a consequence, the ink applied to the water-attracting area Y cannot take up the total amount of water being stored, as a consequence of which it cannot be deposited on area Y of the printing ink and cannot be washed off from the printing plate in a subsequent step.

Since only a certain, defined time period is available during the printing operation, during which an ink applied must take up the film of water lying on the smooth layer Z, but the ink must not take up so much water that it will be deposited on the water-attracting, rough area Y, it was recognized by the inventor that to determine the quality of a printing ink, it must be determined, on the one hand, whether a printing ink does take up water too rapidly, because this ink would otherwise possibly also be deposited on the water-attracting area Y, and the initial water uptake also must not last too long, because the printing ink is otherwise unable to take up the thin film of water and it would also be washed off from the ink-attracting area Z.

According to the process according to the present invention for evaluating the quality of a printing ink, a defined quantity of ink, e.g., 25 mg, is first stirred. Stirring is defined in the sense of the present invention as stirring by means of a suitable rotating element, but also as any other process with which thorough mixing of a liquid can be achieved. If a stirring element is used, this may, e.g., also be suitably moved through the ink without performing a rotary movement in order to thus stir or thoroughly mix the ink. It is also possible to move an ink container with or without a stirring element in it in a suitable manner, e.g., to rotate it or to repeatedly tilt it somewhat to the side in order to stir the ink. The force to be applied or a torque to be applied during the stirring or the necessary output or energy is now measured. This may be performed, e.g., by measuring the torque in the case of a stirring element introduced into the ink. However, depending on the stirring process employed, it is also possible to measure other forces or torques occurring. After the ink has been stirred for a certain time, preferably after the torque to be applied has stabilized, a defined amount of moistening agent, e.g., 1 g to 50 g tap water or distilled water, is added to the ink within a short time, preferably all at once, so that a large quantity of water is suddenly available. This approximately corresponds to the conditions occurring during the printing operation, when the ink is applied to the printing plate within a very short time and if the ink is suitable, it takes up the water so rapidly that it is deposited on the smooth, ink-attractive area Z, but the ink does not take up so much water that it would be deposited on the water-attracting area Y. For example, the water uptake behavior of the ink is determined in the process according to the present invention on the basis of the measured force to be applied during stirring. Immediately after the rapid supply of the defined amount of water, the ink and the water are still in the segregated state, so that the ink-water mixture can be stirred easily. If a stirring element is used for stirring, it can be seen that the torque collapses in most inks immediately after the addition of the defined quantity of water, because these inks cannot take up the water immediately. If no collapse or no appreciable collapse of the torque can be measured, this indicates that the ink has taken up the water added very rapidly. Such an ink would be unsuitable for a printing process, because this ink with very good and rapid water uptake behavior would also be deposited on the water-attracting area Y. If the torque collapses, it can be observed in the course of time, usually after a few minutes, that the torque rises again, i.e., the water added is gradually taken up by the ink sample being investigated. Whether the ink can take up the water added after a preset time and is thus suitable for the printing process or whether the torque collapses for too long, from which poor water uptake behavior of the ink can be inferred, can be determined from the increase in the torque. Such an ink would not be deposited on the ink-attracting smooth area Z of a printing plate, either, because this ink is unable to take up even the thin film of water present on the ink-attracting smooth area Z within the time available during the printing process and is thus unable to be deposited on the ink-attracting area Z, but it would be washed off from this area. Thus, the process according to the present invention can provide information on the rate of water uptake of an ink after the ink suddenly comes into contact with a predetermined quantity of water or is mixed with same. It is thus possible, e.g., to plot diagrams which represent quantitative information on the force to be applied or the torque to be applied during the stirring of the ink overtime, where, in particular, the time period after the rapid addition of the defined quantity of water, the so-called water shock, is of particular significance. Examples of such diagrams are shown in FIGS. 1 through 10 and will be described later.

Even though curves of the measured torque, which were determined in the exemplary embodiments according to FIGS. 1 through 10, are shown, it shall be noted that the present invention is not limited to the examples shown. Depending on the quantity of ink being tested, the quantity of water added, the stirring process, the temperature or other parameters, other characteristics can be obtained, in which the shape of the curve of an ink suitable for the printing process is different. However, a curve different from that for a poor printing ink can always be obtained, in general, for a good printing ink by the process according to the present invention, and the characteristic features of the curves may be optionally determined by tests.

The ink is preferably stirred with a rotating element, especially a stirrer, which is introduced into a container, in which the ink is located. The stirring element may be placed, e.g., in the upper area of the ink sample filled in, i.e., a stirring element performs a stirring movement, e.g., only in the upper area of the ink filled in and does not extend to the bottom of the ink container, so that the stirring element performs a stirring movement predominantly in the contact area between water and ink during the sudden introduction of water before the mixing process takes place.

The stirring of the ink sample is advantageously carried out continuously without and/or with moistening agent added, i.e., for example, at a constant speed of rotation. As an alternative, stirring may also be performed at first at a first, e.g., higher rate until, e.g., the torque to be applied becomes approximately constant and the ink is uniformly liquefied, after which the stirring is then performed at a second, e.g., lower rate in order to obtain a better time resolution of the force, torque or energy curve measured.

The ink sample is especially stirred first at a first speed of rotation during a first time period, e.g., for 2 minutes at 1,200 rpm, after which the speed of rotation is changed, especially reduced, e.g., to 300 rpm, for the further process in order to obtain a better time resolution of the characteristics. If stirring is carried out at a high speed of rotation after the addition of the moistening agent, more rapid uptake of the moistening agent by the ink sample takes place because of the better mixing. However, if the ink sample is stirred first at a higher speed of rotation in order to obtain a defined initial state, e.g., in order to liquefy the ink based on the thixotropic behavior of the ink sample, the rate of water uptake can be reduced by lowering the speed of rotation, so that a better time resolution is obtained. For example, it was determined in a test actually performed that the difference between the rates of water uptake by two inks at 1,200 rpm was approx. 20%, whereas the rate of water uptake differed by a factor of 10 at a speed of rotation of 300 rpm, i.e., more accurate information can be obtained with the process according to the present invention at lower speeds of rotation or slower stirring operations.

The temperature of the ink sample can preferably be set or regulated, e.g., by means of a thermostat or a regulated heating element coupled with a temperature sensor in order to always perform measurements in a preset, preferably constant temperature range. In particular, the measurement is preferably carried out in the temperature range of 20° C. to 60° C., advantageously 30° C. to 50° C. and especially in the range of 40° C.

It is advantageous to add the total, defined quantity of moistening agent to the ink sample only when the force to be applied during the stirring or a torque and/or the temperature is constant. It was found in practical experiments that sufficiently constant values are reached for the temperature and for the force to be applied or a torque after about 3 to 5 minutes.

More moistening agent is advantageously added at a continuous rate after the one-time addition of a defined quantity of moistening agent after a preset time period, so that the saturation limit of the ink can be determined, i.e., the point in time at which the torque collapses, is determined, so that the maximum uptake capacity of the ink for moistening agent, i.e., the quantity of moistening agent that can be taken up per quantity of ink can be calculated from this. As was described above, it is possible to determine in the case of continuous addition of moistening agent whether the wet viscosity of an ink increases or decreases, i.e., whether the viscosity of an ink increases or decreases during the slow addition of moistening agent.

According to another aspect of the present invention, it is possible to determine the moistening agent or water content of an ink sample, which was taken, e.g., from a running printing process, in order to obtain from this data on the course of the water uptake during the printing process. Consequently, a fresh ink is used at the beginning of a printing process, and this fresh ink can come into contact with moistening agent in different areas during the printing process and it can take up different quantities of moisture. If, e.g., an ink sample is taken from a printing plate at a defined point of the printing process, it can be determined by determining the moistening agent content in this ink sample whether this ink sample is suitable for the printing process or whether it has led or will lead to unsatisfactory printing results, e.g., because of a too rapid or too slow uptake of moistening agent. The saturation limit of the fresh ink is first determined according to the present invention by, e.g., supplying water continuously to an ink being stirred as described above until this ink can no longer take up water and the force to be applied during the stirring decreases because of the dilution of the saturated ink by excess moistening agent, i.e., for example, the stirring torque collapses. The saturation limit of the fresh ink thus determined is used as a reference variable for the later calculation. Moistening agent is added to the ink sample being tested according to the present invention while stirring is continued until the saturation limit of the ink sample being tested is reached. This may again be performed, e.g., as described above by measuring the force to be applied during a stirring operation. The amount of moistening agent or water that has already been taken up by the ink sample prior to the addition of more moistening agent can be calculated from these two values determined, i.e., the saturation limit of the fresh ink and the quantity of moistening agent added to the ink sample. If, for example, an ink sample of 30 g is tested, for which the speed of rotation is reduced to 300 rpm after an initial stirring at a speed of, e.g., 1,200 rpm for a period of 2 minutes, and the continuous addition of moistening agent is started at a rate of 2.5 g per minute after the stirring for 3 minutes at 300 rpm until the torque collapses, the percentage water content in the ink sample can be determined from the following formulas (1) through (4):

$$\text{Weight}_{(ink\ sample+water)} = 30\ g + \text{injection time} * 2.5\ g\ \text{per minute} \quad (1)$$

$$\text{Water}_{(at\ saturation\ limit)} = \text{saturation limit}_{(of\ fresh\ ink\ sample)}/100 * \text{weight}_{(ink\ sample+water)} \quad (2)$$

$$\text{Water}_{(in\ original\ ink\ sample)} = \text{Water}_{(at\ saturation\ limit)} - \text{injection time} * 2.5\ g\ \text{per minute} \quad (3)$$

$$\text{percentage water content in ink sample} = (\text{water}_{in\ original\ ink\ sample}/30\ g) * 100 \quad (4)$$

In particular, the saturation limit of an ink shall be above 30% according to this test procedure in order to obtain good printing results.

The device according to the present invention for evaluating the quality of a printing ink has a container, into which the ink to be tested can be introduced. Furthermore, a stirring device is provided, which may be, as was explained above, e.g., a stirring element that can be introduced into the container or a rotating and/or tilting device for the container with or without a stirring element introduced into it. The force to be applied for stirring the ink present in the container or a torque to be applied or an energy or output to be applied is measured by a measuring device and is preferably plotted in the form of a diagram over a time axis. A moistening agent feed and a control for the moistening agent feed are preferably provided according to the present invention, the control being designed such that a defined quantity of moistening agent can be added to the ink present in the container at a defined point in time. Qualitative data can then be obtained on the suitability of the ink for printing, especially offset printing, on the basis of the force or torque curve determined by the measuring device after the addition of the moistening agent.

A temperature-regulating device, especially a thermostat with a temperature sensor and a heating device, is preferably provided in order to bring the container for the ink to a suitable temperature, so that measurements can also be carried out in a defined temperature range.

The control is advantageously designed such that one or more of the above-described process steps, for example, the continuous addition of a moistening agent after the water shock, i.e., after the one-time addition of a defined quantity of moistening agent, the setting of the range of speeds of rotation for the initial stirring of the ink at a first, higher speed of rotation and for the further stirring of the ink at a second, lower speed of rotation, at which the moistening agent is added, etc., can be carried out with the device according to the present invention.

A device for carrying out the above-mentioned process, especially combined with a printing press, is also proposed according to the present invention, wherein the above-described device for determining the quality of a printing ink is provided combined with a printing press, especially an offset printing press, so that an ink fed to the printing press is tested or analyzed automatically before and/or during the printing process and the setting of the printing press can be automatically changed depending on the test result.

According to another aspect of the present invention, an ink processing process and an ink processing device is created, which can automatically test an ink being fed according to the above-described process and optionally add suitable ink additives to the ink in order to adapt this ink to the printing process, i.e., to make this ink suitable for the printing process. Ink additives which increase or decrease the water uptake capacity and/or the rate of water uptake of an ink may be used for this purpose. Reference is made, e.g., to the ink additives Colorthix and Colorstabil from the firm of Vegra, which can modify the moistening agent uptake capacity of an ink. Consequently, it is also possible according to the present invention to introduce an ink that is unsuitable per se into the ink processing device, which adds to the ink a suitable ink processing agent, e.g., colored pigments, binders, diluents, e.g., water, solvent or other additives, e.g., resin as a function of the test result, i.e., for instance, a torque curve deviating from an ideal curve of the ink being tested in order to make this ink suitable for use for the subsequent printing process. This process may also be designed as a self-learning process, e.g., using a neuronal network.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
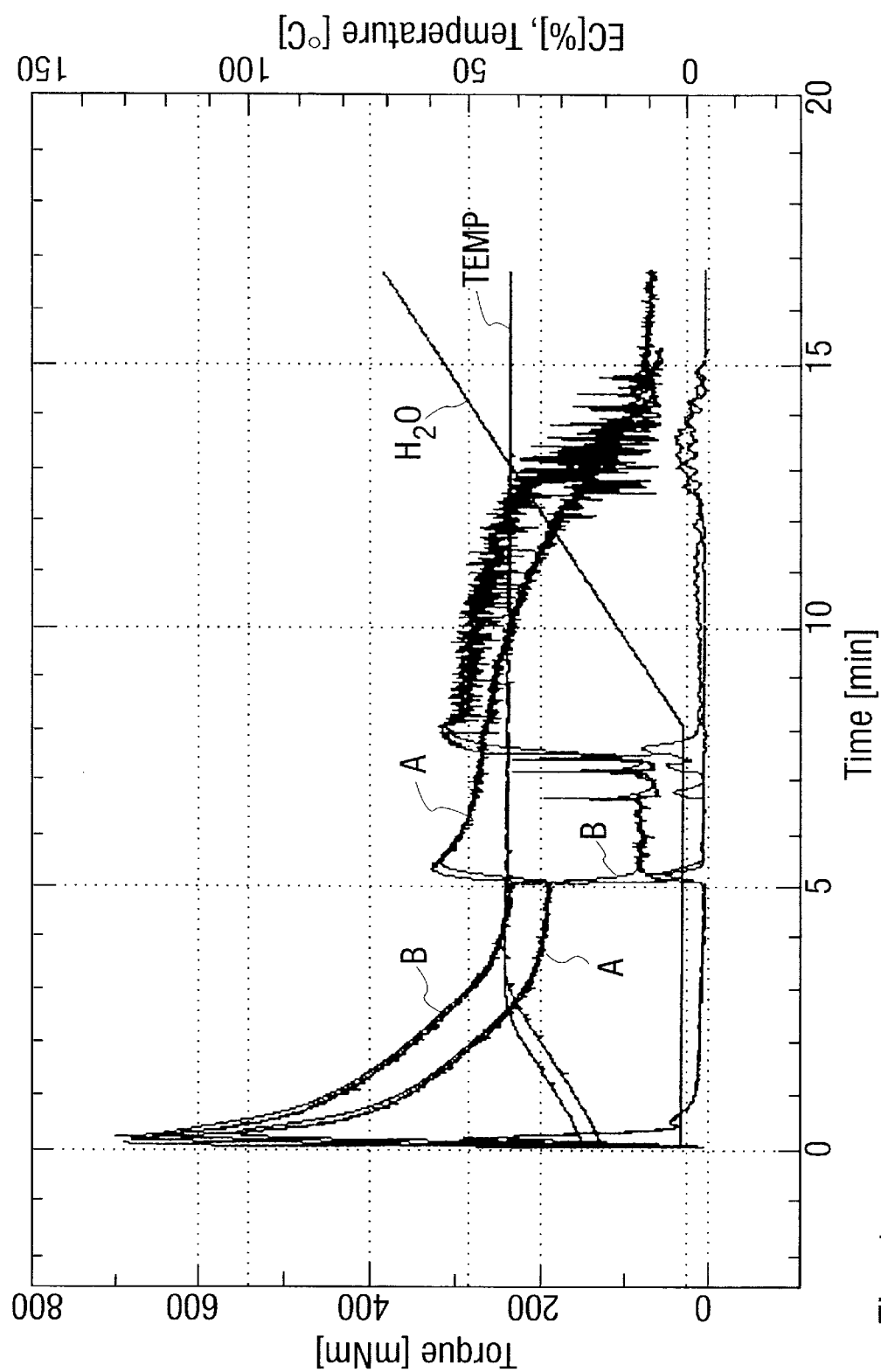
FIG. 1 is a diagram showing a test result for two inks with different water uptake capacities.
Figure 13:
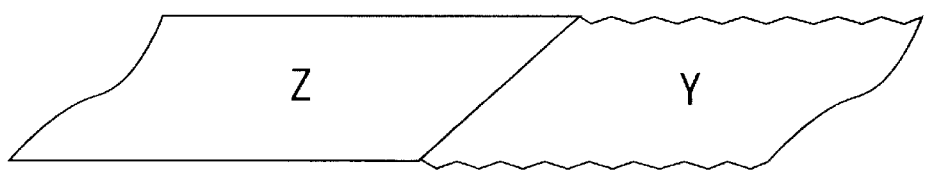
FIG. 13 schematically shows the surface of a printing plate with ink-attracting area Z and water-attracting area Y.

Referring to the drawings in particular, FIG. 1 shows, in principle, the curve of the torque in mNm over time in the case of an ink sample of 25 g, which is stirred at a speed of 1,200 rpm during the first 5 minutes until the torque becomes constant at about 220 mNm, injecting 7.5 g of moistening water after 5 minutes. It is seen that ink A has taken up the moistening water fed in very rapidly and will consequently probably lead to problems during offset printing. The torque collapses in the case of the ink B being tested to a value of about 80 mNm immediately after the addition of the moistening water and rapidly increases again about 2 to 3 minutes after the addition of the moistening agent, i.e., ink B displays a water uptake behavior favorable for offset printing, and it will consequently be deposited sufficiently rapidly on the ink-attracting area Z of the printing plate shown schematically in FIG. 13 and will not be deposited on the water-attracting area Y. Water is added continuously 8 minutes after the beginning of the stirring operation, i.e., 3 minutes after the addition of 7.5 g of moistening water until the saturation limit of inks A and B is reached, i.e., the torque collapses nearly completely.

It was found, in general, that the torque collapsed during the first-time addition of a moistening agent in the case of good printing inks, i.e., it rapidly dropped to a certain value, so that such a curve section as an indicator argues in favor of good ink quality. The torque rises again after a rather short time in the case of a good printing ink.

Figure 2:
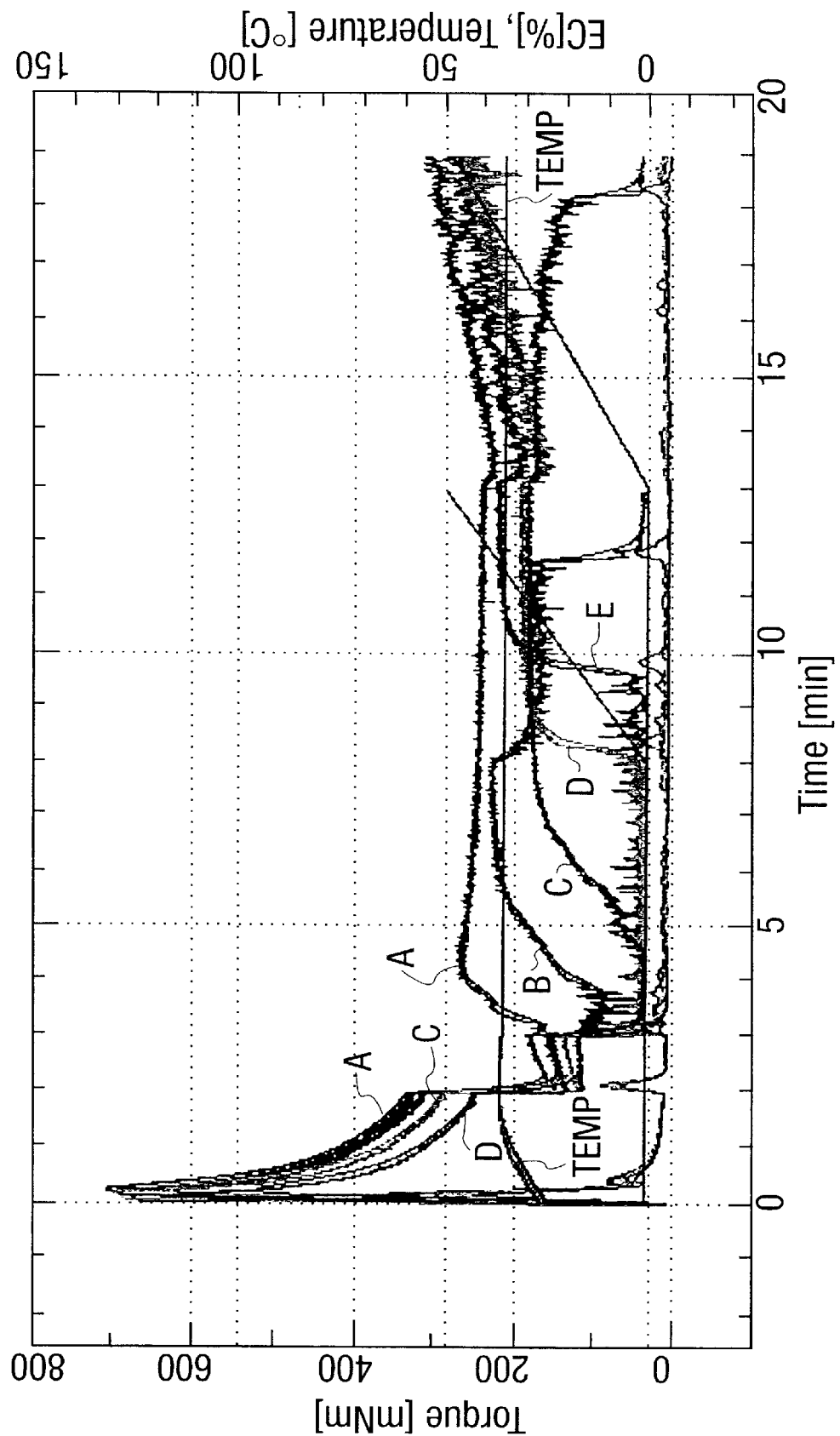
FIG. 2 is a diagram showing an ink analysis of a first set of color plates used on a first printing press.
Figure 3:
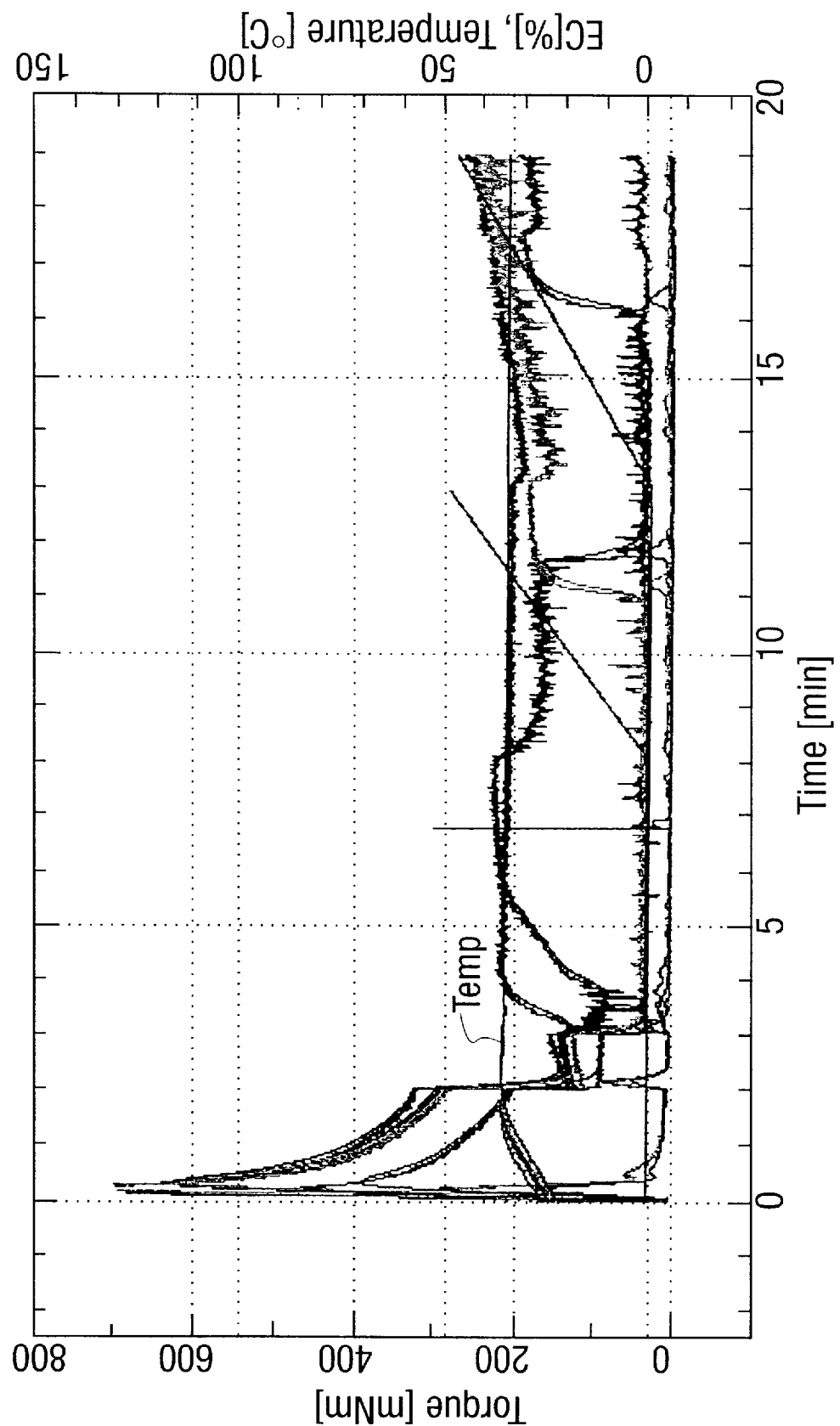
FIG. 3 is a diagram showing an ink analysis of a second set of color plates used on the first printing press.

FIGS. 2 and 3 show the testing of different sets of color plates used in a printing press installed in Guangzhou. As is apparent from the diagram, the initial speed of rotation was lowered after about 2 minutes, and the moistening agent was added after about 3 minutes. As can be recognized from the analytical curve being shown for ink A, this ink takes up the moistening agent too rapidly and is thus rather unsuitable for offset printing. Unlike ink A, inks B and C do not take up the moistening agent added immediately but after a certain period of time, and both were suitable for offset printing. Ink D has a poor uptake capacity for moistening agent and, like ink E, should not be used for offset printing. The printing press operated with the set of color plates shown in FIG. 2 was running error-free for a short time only after the setting. Based on the diagrams of the analysis of the inks used last, which are shown in FIG. 3, it was possible to demonstrate that the supplier of the printing inks used had changed the composition of these printing inks, so that these printing inks take up moistening agent either too rapidly or too slowly, so that the incorrect function of the printing press was able to be unambiguously attributed to the impairment in the quality of the printing inks used. There are no curves in which the torque collapses rapidly after the addition of moistening agent and rises again shortly thereafter.

Figure 4:
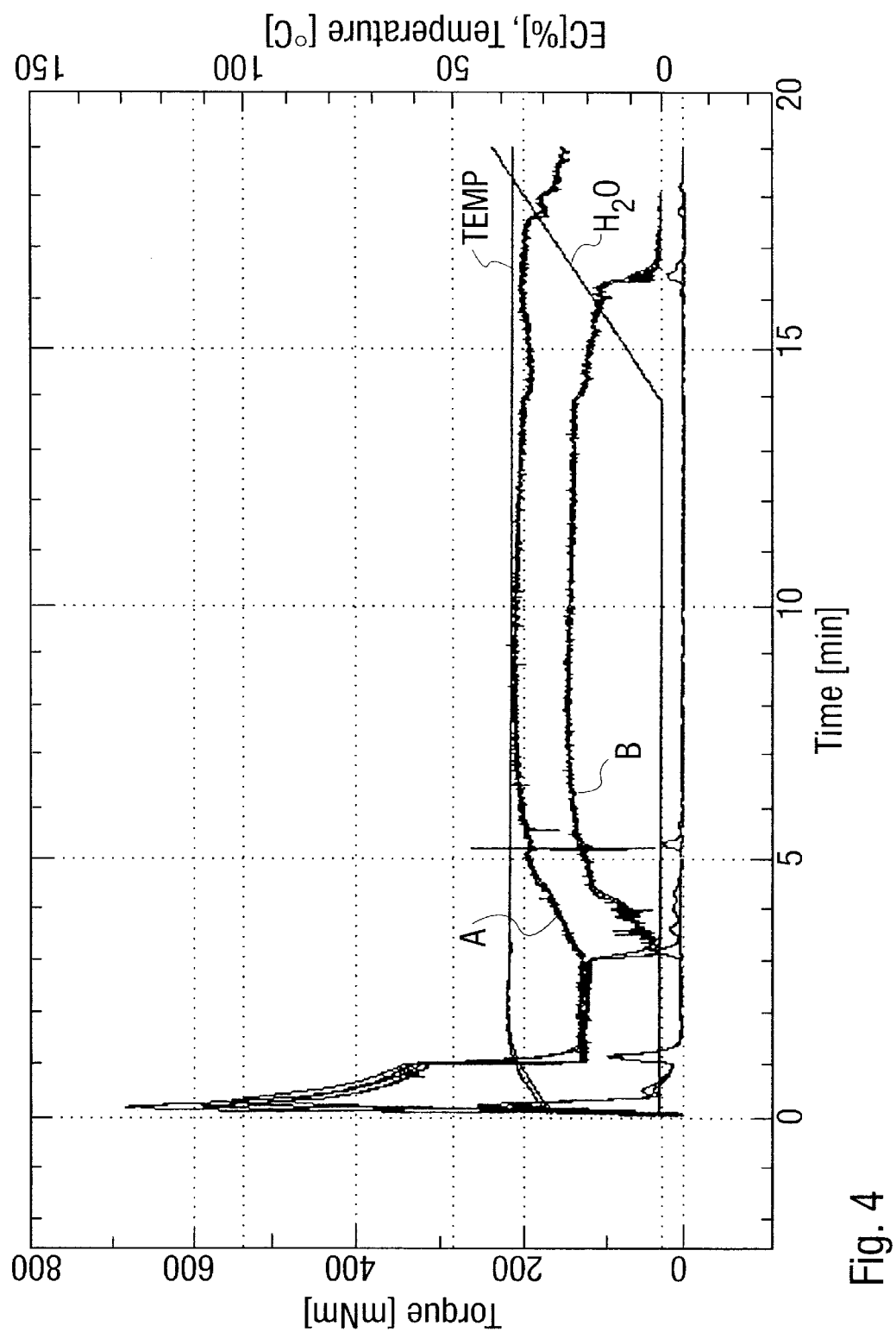
FIG. 4 is a diagram showing an ink analysis for a second printing press.

FIG. 4 shows the result of another analysis of printing inks used in a printing press installed in Münster; it can be seen here that ink A takes up the moistening agent too rapidly and therefore leads to insufficient printing results, whereas ink B is well suited for offset printing.

Figure 5:
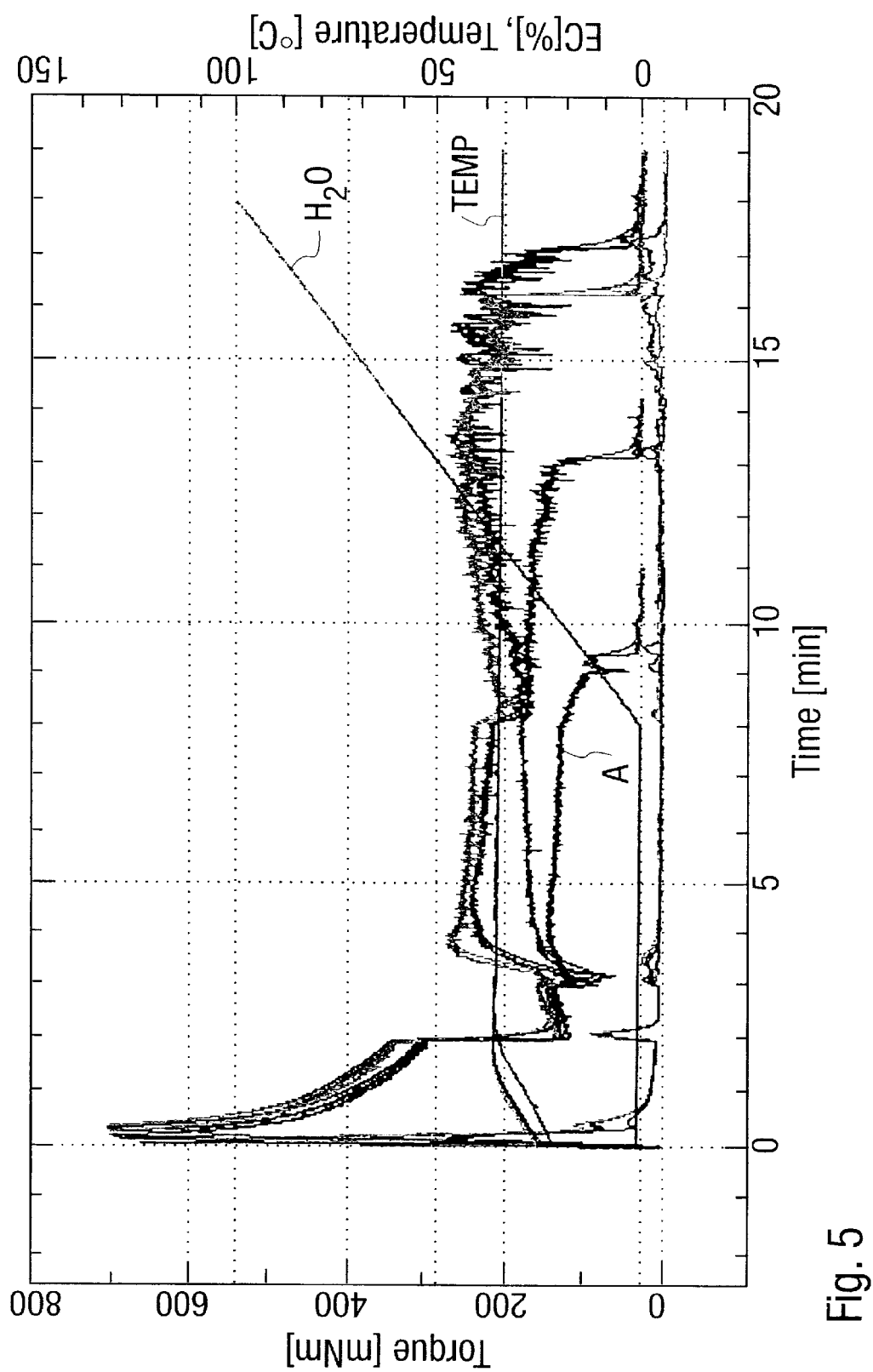
FIG. 5 is a diagram showing, together with FIG. 6, the ink analysis for a third printing press.
Figure 6:
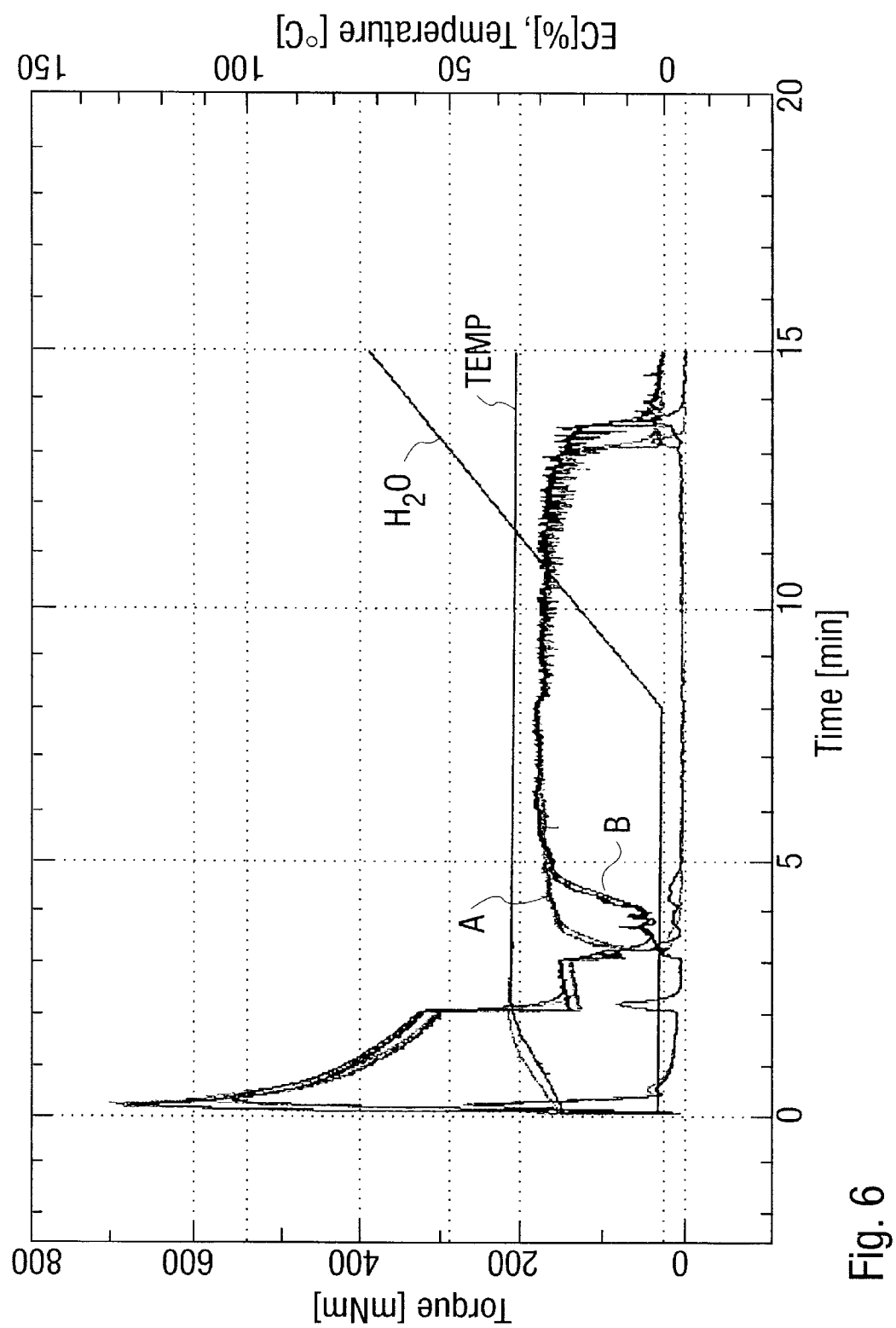
FIG. 6 is a diagram showing, together with FIG. 5, the ink analysis for a third printing press.

FIGS. 5 and 6 show analytical results for different sets of color plates in a printing press, where problems occurred especially with the ink identified as A. This ink has a very low saturation limit, which led to problems especially at high press speeds above 30,000 cylinders per hour. The torque of ink A already collapsed at a moistening agent content of 30%, which proved to be too low for offset printing. It was empirically determined that the saturation of an ink should be above 30% of moistening agent in order to obtain satisfactory printing results. FIG. 6 shows the testing of two inks used on the same press, where ink A takes up moistening agent too rapidly and led to poor printing results. In the case of ink B tested, the torque collapsed for a short time of about one minute after the addition of moistening agent and rose again thereafter. This ink yielded good printing results.

Figure 7:
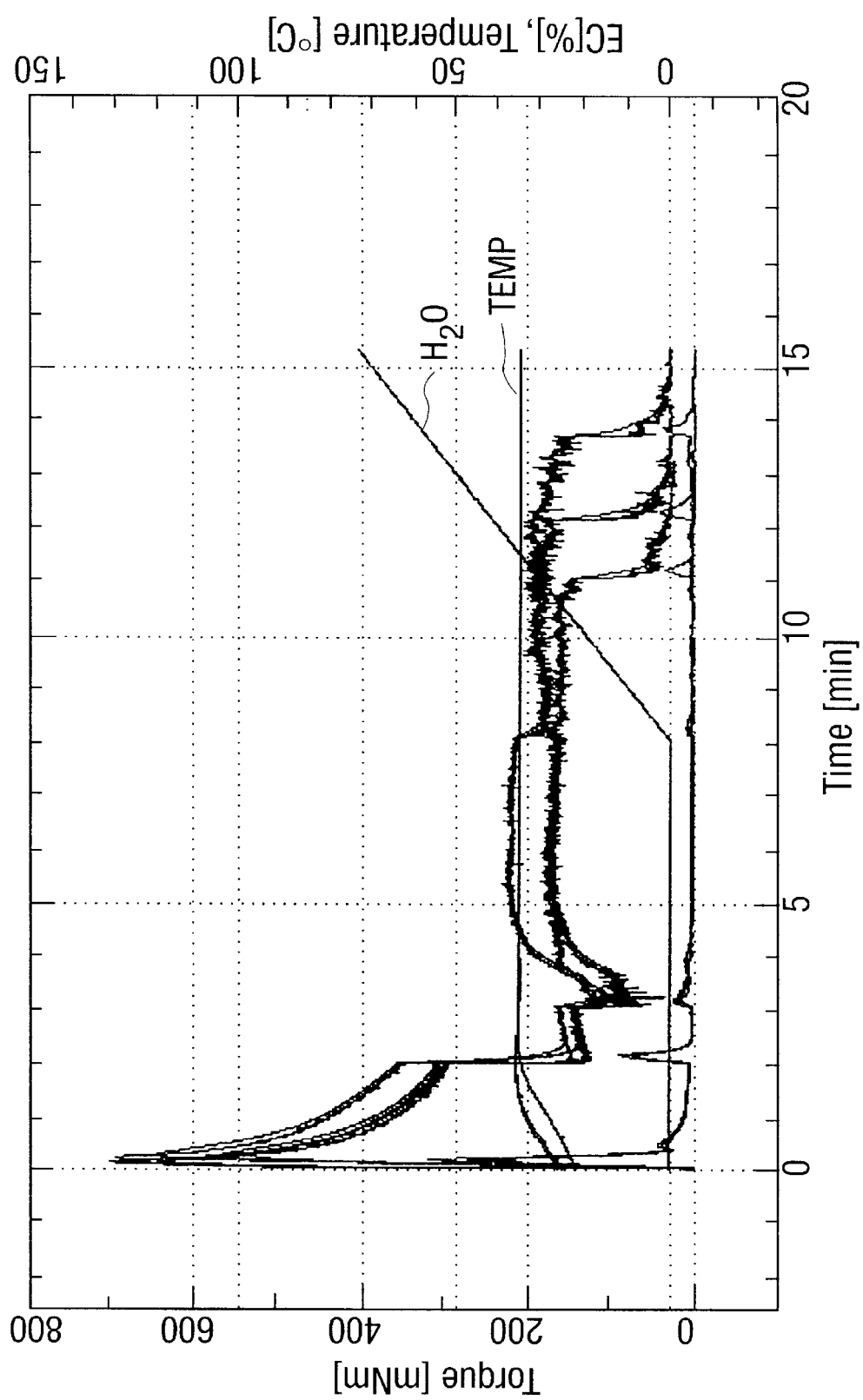
FIG. 7 is a diagram showing, together with FIG. 8, the ink analyses of two sets of color plates for a printing press with a short inking mechanism.
Figure 8:
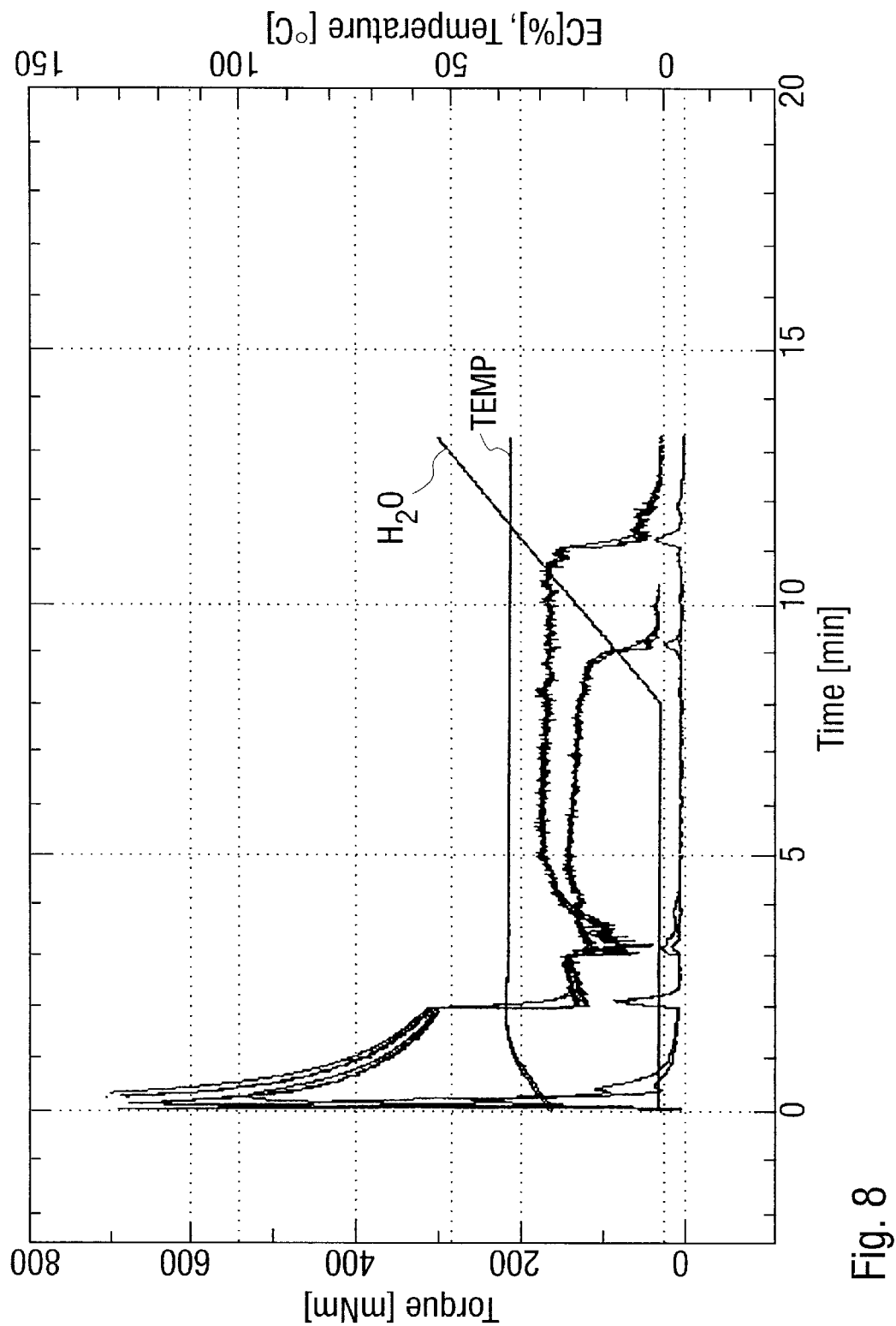
FIG. 8 is a diagram showing, together with FIG. 7, the ink analyses of two sets of color plates for a printing press with a short inking mechanism.

FIGS. 7 and 8 show the analyses of two sets of color plates from the same supplier, which were used in a short inking mechanism, as a result of which it was possible to demonstrate that the quality of ink supplied by the supplier was subject to great variations and incorrect behavior of the printing press was thus caused by inks of an inferior quality.

Figure 9:
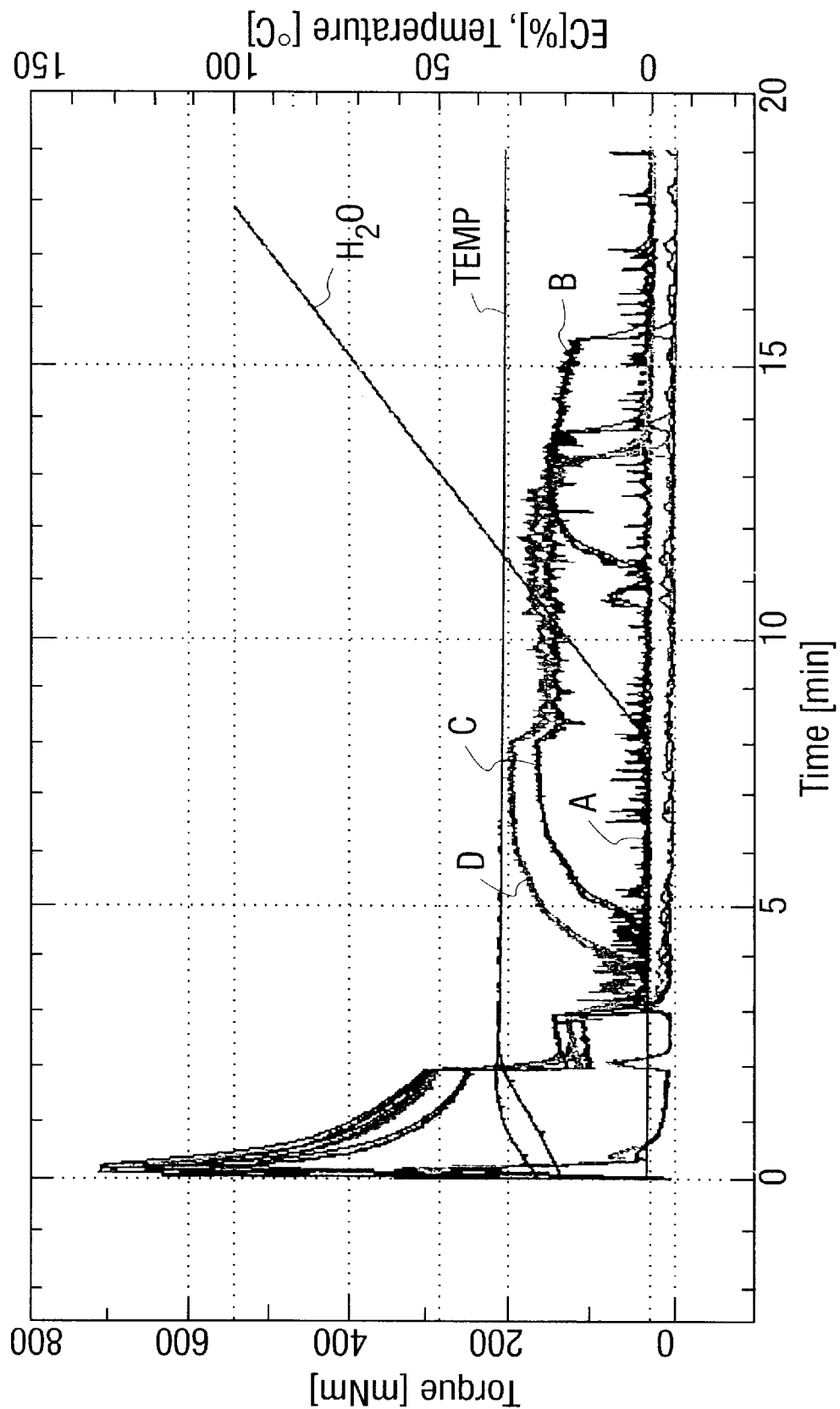
FIG. 9 is a diagram showing an analytical result for the preliminary testing of the suitability of a set of color plates for a printing press with a split inking mechanism.

FIG. 9 shows the preliminary testing of a set of color plates for a printing press with split inking mechanism, where it had been determined by the preliminary testing that the inks A and B used would lead to problems because of the excessively long torque collapse and consequently too poor uptake capacity for moistening agent, whereas inks C and D should be able to be used without problems.

Figure 10:
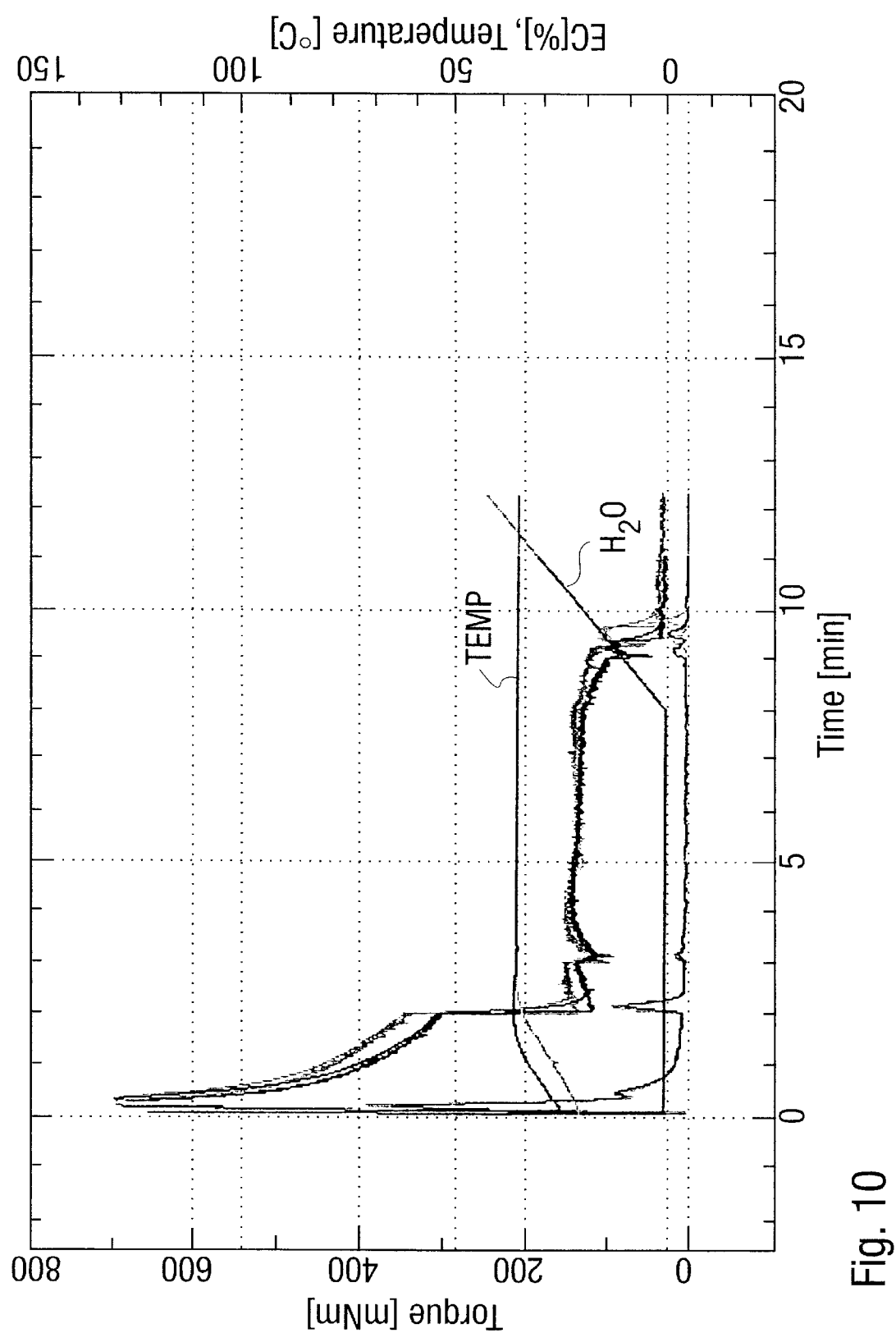
FIG. 10 is a diagram showing an ink analysis in case of mists and poor delivery in the ink duct.
Figure 11:
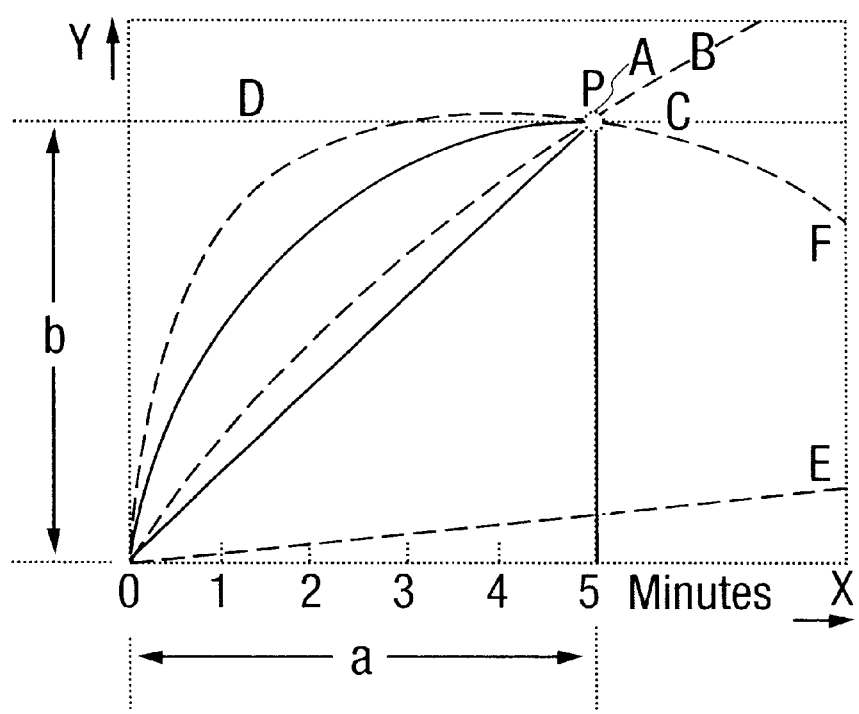
FIG. 11 is a diagram showing a diagram of the water tolerance test according to the Surland model.
Figure 12:
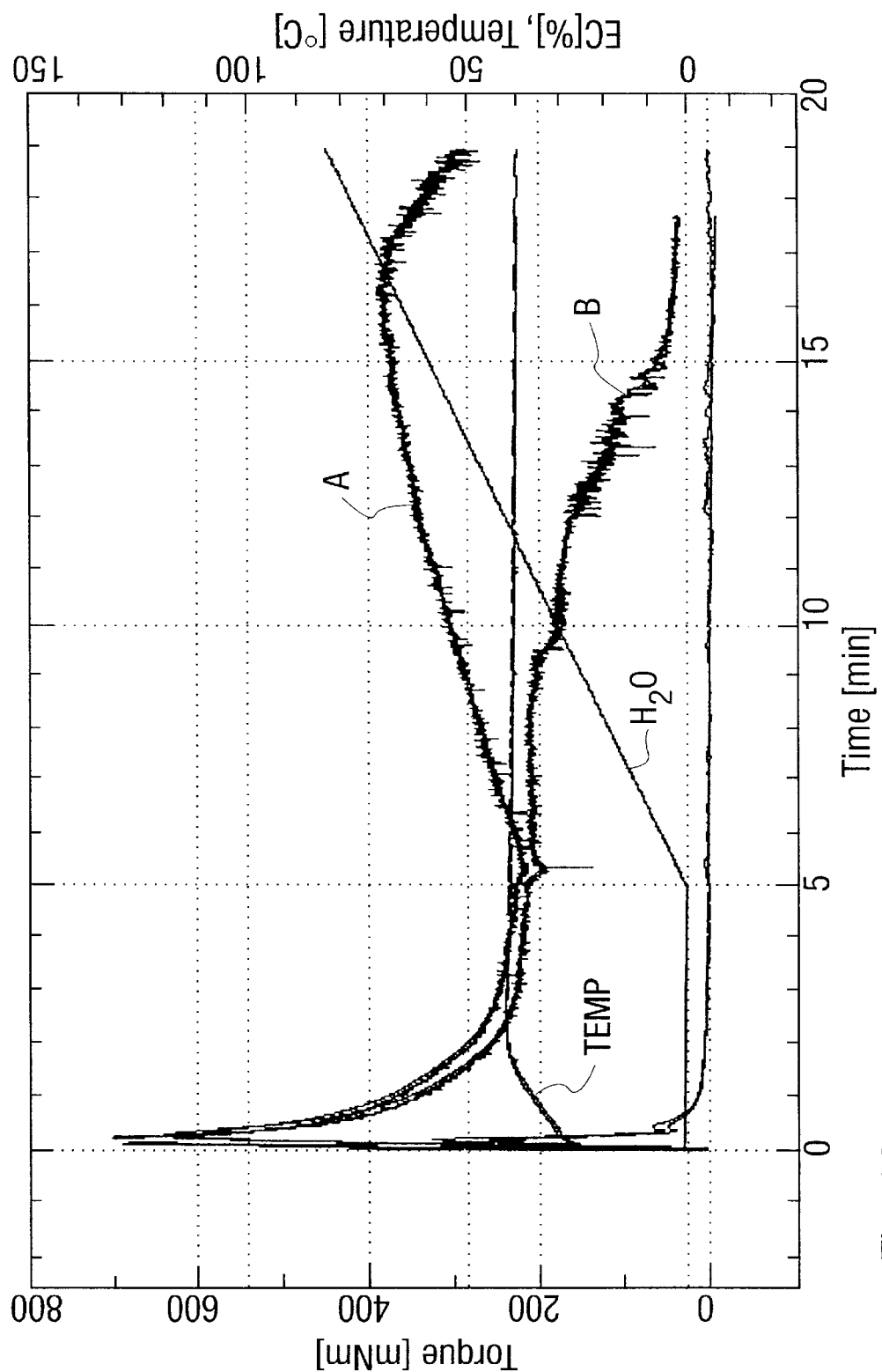
FIG. 12 is a diagram showing a diagram of a prior-art ink analysis process.

FIG. 10 shows the ink analysis in the case of mists and poor delivery in the ink duct. It was possible to establish that the saturation limit of the inks tested was too low, because the torque collapses immediately after the continuous supply of water and it must be increased in order to achieve printing of high quality.

Figure 14:
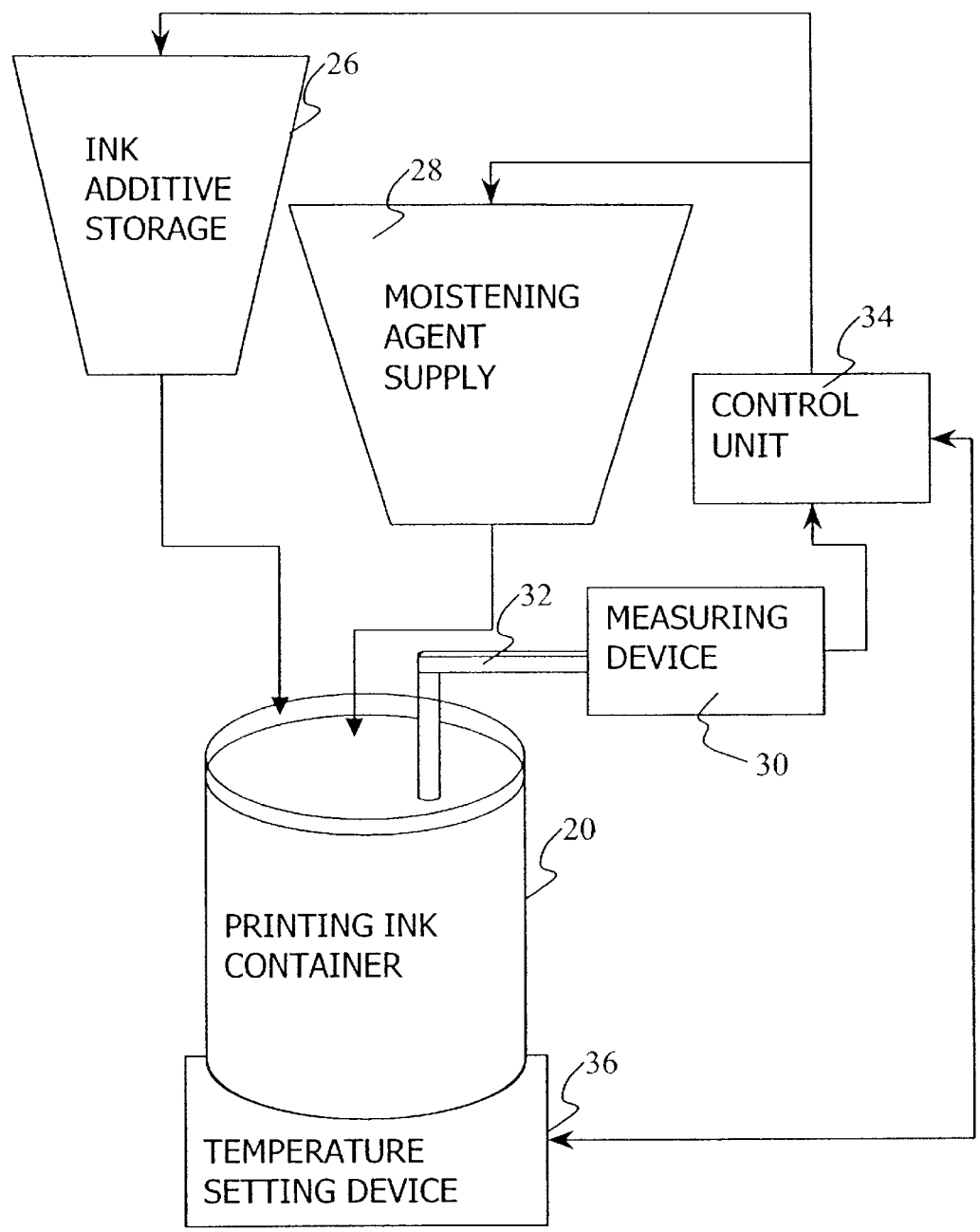
FIG. 14 is a schematic view of the device for evaluating the quality of a printing ink according to the invention.

FIG. 14 shows the device for evaluating the quality of a printing ink according to the invention. The device includes the printing ink container 20 and a stirring device 32. The stirring device 32 stirs the ink in container 20 as described above. The stirring device 32 is connected to measuring device 30 for measuring the force or the torque applied by the stirring device 32. The device for evaluating the quality of a printing ink also includes a control device 34 which times (clocks) the stirring process for each stirring rate and controls the moistening agent supply 28 to introduce the moistening agent into the container 20 at a defined point during the stirring process. The control device 34 also controls at the rate of stirring. Different stirring rates may be used for different phases during the procedure, as described above. The control device 34 also controls a temperature setting device 36 so as to maintain the temperature of the ink at a substantially constant value such that it does not vary during the process. The control device 34 also controls ink additives added to the ink from ink additive storage unit 26. Ink additives are added to improve the properties of the ink. The control device 34 can provide an analysis of the ink to determine what ink additives, if any should be added.

While specific embodiments of the invention have been shown and described in detail to illustrate the application of the principles of the invention, it will be understood that the invention may be embodied otherwise without departing from such principles.

What is claimed is:

1. A process for evaluating the quality of a printing ink, the process comprising the steps of:
   stirring a defined quantity of the printing ink;
   applying a force, energy or a torque during said stirring;
   measuring the applied force, energy or torque; and
   adding a defined quantity of moistening agent to the ink at a defined time;
   adding additional moistening agent continuously at a preset rate after a preset time period after said adding of the defined quantity of moistening agent.

2. A process in accordance with claim 1, wherein the stirring is carried out by one of rotating a rotating element, displacing a stirring element, rotating an ink container, and tilting an ink container;
   the defined quantity of moistening agent is added to the ink substantially all at once.

3. A process in accordance with claim 1, wherein the ink is stirred continuously during the process.

4. A process in accordance with claim 1, wherein stirring is carried out at first at a first rate and then at a second rate, where the second rate is a lower rate than the first rate.

5. A process in accordance with claim 1, wherein the temperature of the ink is substantially does not vary during the process.

6. A process in accordance with claim 1, wherein the moistening agent is added only when the force to be applied during the stirring or the torque to be applied is approximately constant.

7. A process for determining the moistening agent content in an ink sample, the process comprising:
   a) determining the saturation limit of a fresh ink;
   b) adding a moistening agent to the ink sample during ongoing stirring;
   c) measuring a point in time at which the force to be applied for stirring or the torque to be applied drops below a predetermined limit; and
   d) the moistening agent content is determined from the determined saturation limit of the fresh ink and the time period determined.

8. A device for evaluating the quality of a printing ink, the device comprising:
   a container having a defined quantity of the printing ink;
   a stirring device for stirring ink filled into the container;
   a measuring device for measuring the force or the torque applied by the stirring device;
   a moistening agent supply; and
   a control device for actuating the moistening agent supply such that a preset quantity of moistening agent is introduced into the container at a defined point in time, said a control device also actuating the moistening agent supply such that additional moistening agent is introduced into the container at a predetermined rate after a time delay from said defined point in time.

9. A device in accordance with claim 8, further comprising a temperature-setting device at the container for setting the temperature of the ink.

10. A device in accordance with claim 8, wherein the control device controls stirring the defined quantity of the printing ink and the stirring is carried out by rotating one of a rotating element, displacing a stirring element, rotating an ink container, tilting an ink container;
   the defined quantity of moistening agent is added to the ink substantially all at once.

11. A device in accordance with claim 8, wherein the control device controls the ink is stirred continuously during the process.

12. A device in accordance with claim 8, wherein the control device controls stirring first at a first rate and then at a second rate, where the second rate is a lower rate than the first rate.

13. A device in accordance with claim 9, wherein the temperature of the ink is controlled to substantially not vary.

14. A device in accordance with claim 8, wherein the control device controls the moistening agent addition so it is only added when the force to be applied during the stirring or the torque to be applied is approximately constant.

15. A device in accordance with claim 8, wherein the control device determines the saturation limit of a fresh ink, controls the addition of the moistening agent to an ink sample during ongoing stirring and measures a point in time at which the force to be applied for stirring or the torque to be applied drops below a predetermined limit and determines the moistening agent content from the determined saturation limit of the fresh ink and the time period determined.

16. A device in accordance with claim 8, further comprising a storage device for ink additives, which change the uptake capacity of the ink for moistening agent, and with a control, which adds the ink additives to the ink as a function of an analytical result.

17. A process for automatic ink processing according to claim 1, further comprising analyzing the ink and adding ink-improving additives as a function of the analytical result.

18. A process for automatic ink processing according to claim 7, further comprising analyzing the ink and adding ink-improving additives as a function of the analytical result.

19. A process in accordance with claim 1, wherein:
   said measuring is performed before, during and after said adding of said defined quantity of moistening agent and said adding of the moistening agent at the preset rate;
   a comparison of said applied force, energy or torque before, during and after said adding is performed;
   an indication of the quality of the printing ink is provided based on said comparison.

20. A process for evaluating the quality of a printing ink, the process comprising the steps of:
   stirring a predefined quantity of the printing ink;
   measuring a first force required by said stirring;
   adding a predefined quantity of moistening agent to the ink at a predefined time during said stirring;
   measuring second force required by said stirring after said adding of the moistening agent;
   comparing said first force with said second force;
   indicating a quality of the printing ink based on said comparing.

21. A process in accordance with claim 20, further comprising:
   adding additional moistening agent to the printing ink at a predetermined rate, said adding of the additional agent being performed after a time delay from said adding of said predefined quantity;
   measuring a third force required by said stirring during said adding of the additional moistening agent at said predetermined rate;
   comparing said third force with a quantity of the moistening agent added from said step of adding of the additional moistening agent;
   indicating an additional quality of the printing ink based on said comparing of said third force and said quantity of additional moistening agent.

22. A process in accordance with claim 20, wherein:
   said stirring is carried out at a first rate and then at a second rate, where the second rate is a lower rate than the first rate.

23. A process in accordance with claim 20, wherein:
   the moistening agent is added only when the force applied during said stirring is substantially constant.

* * * * *